(12) United States Patent
Small

(10) Patent No.: US 7,001,964 B2
(45) Date of Patent: Feb. 21, 2006

(54) SELECTIVE ISOMERIZATION AND LINEAR DIMERIZATION OF OLEFINS USING COBALT CATALYSTS

(75) Inventor: Brooke L. Small, Kingwood, TX (US)

(73) Assignee: Chevron Phillips Chemical Company, LP, The Woodlands, TX (US)

(*) Notice: Subject to any disclaimer, the term of this patent is extended or adjusted under 35 U.S.C. 154(b) by 133 days.

(21) Appl. No.: 10/389,312

(22) Filed: Mar. 14, 2003

(65) Prior Publication Data

US 2004/0068072 A1 Apr. 8, 2004

Related U.S. Application Data

(63) Continuation-in-part of application No. 10/264,730, filed on Oct. 4, 2002.

(51) Int. Cl.
*C08F 210/00* (2006.01)

(52) U.S. Cl. .............. 526/348; 526/169; 526/171; 526/172; 526/161; 526/901; 526/130

(58) Field of Classification Search ........... 526/130, 526/161, 169, 171, 172, 901, 348, 348.3, 526/348.5, 348.6, 351
See application file for complete search history.

(56) References Cited

U.S. PATENT DOCUMENTS

| | | | | |
|---|---|---|---|---|
| 4,320,243 | A | 3/1982 | Chauvin et al. | 585/521 |
| 5,955,555 | A | 9/1999 | Bennett | 526/133 |
| 6,063,881 | A | 5/2000 | Bennett | 526/161 |
| 6,103,946 | A | 8/2000 | Brookhart, III et al. | 585/523 |
| 6,291,733 | B1 * | 9/2001 | Small et al. | 585/512 |
| 6,489,497 | B1 | 12/2002 | Brookhart, III et al. | 556/138 |
| 2002/0177744 | A1 | 11/2002 | Small et al. | 585/16 |
| 2003/0149198 | A1 * | 8/2003 | Small et al. | 526/115 |

FOREIGN PATENT DOCUMENTS

| | | |
|---|---|---|
| GB | 1124123 | 8/1968 |
| GB | 1129463 | 10/1968 |

OTHER PUBLICATIONS

*Highly Active Iron and Cobalt Catalysts for the Polymerization of Ethylene*, Brooke L. Small, Maurice Brookhart, and Alison M.A. Bennett, *Journal of the American Chemical Society*, vol., 120, No. 16, Pp. 4049–4050, 1998.
*Iron Catalysts for the Head–to–Head Dimerization of a–Olefins and Mechanistic Implications for the Production of Linear a–Olefins*, Brooke L. Small and A.J. Marcucci, *Organometallics*, vol. 20, No. 26, Pp. 5738–5744, 2001.
International Search Report, PCT/US 03/29158, Feb. 23, 2004; 3 pages.

* cited by examiner

*Primary Examiner*—William K. Cheung
(74) *Attorney, Agent, or Firm*—Conley Rose, P.C.; Rodney B. Carroll; Joe D. Hulett

(57) ABSTRACT

Provided herein is an oligomerization product formed from alpha-olefins having at least three carbon atoms comprising dimers, at least about 80 weight percent of which are linear. In an embodiment, an oligomerization product formed from alpha-olefins having at least three carbon atoms comprises trimers, at least about 20 weight percent of which are linear. In another embodiment, an oligomerization product formed from alpha-olefins having at least three carbon atoms comprises tetramers, at least about 5 weight percent of which are linear. In yet another embodiment, an oligomerization product formed from alpha-olefins having at least three carbon atoms comprises pentamers, at least about 5 weight percent of which are linear.

23 Claims, 2 Drawing Sheets

CG Trace of Propylene Dimers (53% 1-Hexane, Complex Id)

SELECTIVE ISOMERIZATION AND LINEAR DIMERIZATION OF OLEFINS USING COBALT CATALYSTS

CROSS-REFERENCE TO RELATED APPLICATIONS

The present application is a continuation-in-part of U.S. patent application Ser. No. 10/264,730, filed Oct. 4, 2002, entitled "Selective Isomerization and Linear Dimerization of Olefins Using Cobalt Catalysts," which is incorporated herein by reference.

FIELD OF THE INVENTION

This invention is in the field of olefin catalysis. Various olefins are produced by a process employing a tridentate cobalt catalyst.

BACKGROUND OF THE INVENTION

Alpha-olefins, especially those containing about 6 to about 20 carbon atoms, are important items of commerce, with about 1.5 million tons reportedly being produced in 1992. Alpha-olefins are also used as intermediates in the manufacture of detergents, as monomers (especially in linear low density polyethylene), and as intermediates for many other types of products. As a consequence, improved methods of making these compounds are of value.

The dimerization of olefins by transition metal complexes represents an important class of industrially relevant chemistry.[1] For example, ethylene dimerization to 1-butene can provide a source of comonomer in the production of polyethylene;[2] and olefins such as propylene and butene are dimerized to give $C_6$–$C_8$ materials that serve as feedstocks for gasoline blending or alcohol production.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as diethylaluminum chloride (DEAC). In all of these processes significant amounts of branched and/or internal olefins and/or diolefins, are produced. Since in most instances these are undesired, and often difficult to separate from the desired linear alpha-olefins, minimization of these byproducts is sought.

In the field of olefin catalysis, tridentate iron catalysts are known for the production of α-olefins. Examples of these iron catalysts may be found in U.S. Pat. No. 6,103,946, issued Aug. 15, 2000, the disclosure of which is herein incorporated by reference.

Additional cobalt based catalysts useful for the oligomerization of propylene are taught in U.S. Pat. No. 6,063,881, the disclosure of which is herein incorporated by reference.

Currently, there are no known methods to selectively make linear internal olefins or alpha-olefins from propylene.

The development of cobalt catalysts having enhanced selectivity and high productivity in the production of olefins and alpha-olefins is of value.

Thus, it would be a significant contribution to the art to provide cobalt catalysts for the production of olefins which have both good productivity and high selectivity.

SUMMARY OF THE INVENTION

Provided herein is an oligomerization product formed from alpha-olefins having at least three carbon atoms comprising dimers, at least about 80 weight percent of which are linear. In an embodiment, an oligomerization product formed from alpha-olefins having at least three carbon atoms comprises trimers, at least about 20 weight percent of which are linear. In another embodiment, an oligomerization product formed from alpha-olefins having at least three carbon atoms comprises tetramers, at least about 5 weight percent of which are linear. In yet another embodiment, an oligomerization product formed from alpha-olefins having at least three carbon atoms comprises pentamers, at least about 5 weight percent of which are linear. In another embodiment, an isomerization product formed from alpha-olefins having at least four carbon atoms comprises at least about 80 weight percent 2-olefins. In another embodiment, an isomerization product formed from alpha-olefins having at least four carbon atoms comprises at least about 90 weight percent 2-olefins and 3-olefins.

Also provided herein is an oligomerization product formed from alpha-olefins having at least three carbon atoms that includes one or more oligomers selected from the group consisting of dimers, at least about 80 weight percent of which are linear; trimers, at least about 20 weight percent of which are linear; tetramers, at least about 5 weight percent of which are linear; pentamers, at least about 5 weight percent of which are linear; and combinations thereof. In an embodiment, such an oligomerization product undergoes one or more further processing steps. Such further processing steps may be selected from the group consisting of conversion to alcohols, a poly alpha-olefin, a poly internal olefin, or combinations thereof; conversion to a carboxylic acid; conversion to a linear alkyl benzene; conversion to a functional drilling fluid; conversion to an alkyl succinic anhydride; conversion to an olefin sulfonate; conversion to an alkane sulfonate; conversion to an epoxide; feeding as comonomer for production of polyethylene; purification such that the weight percent of one or more of the dimers, trimers, tetramers, and pentamers therein is increased; metathesis with ethylene to produce an alpha-olefin from one or more of the dimers, trimers, tetramers, and pentamers having an internal double bond; and combinations thereof.

DETAILED DESCRIPTION OF THE INVENTION

Figure 1:
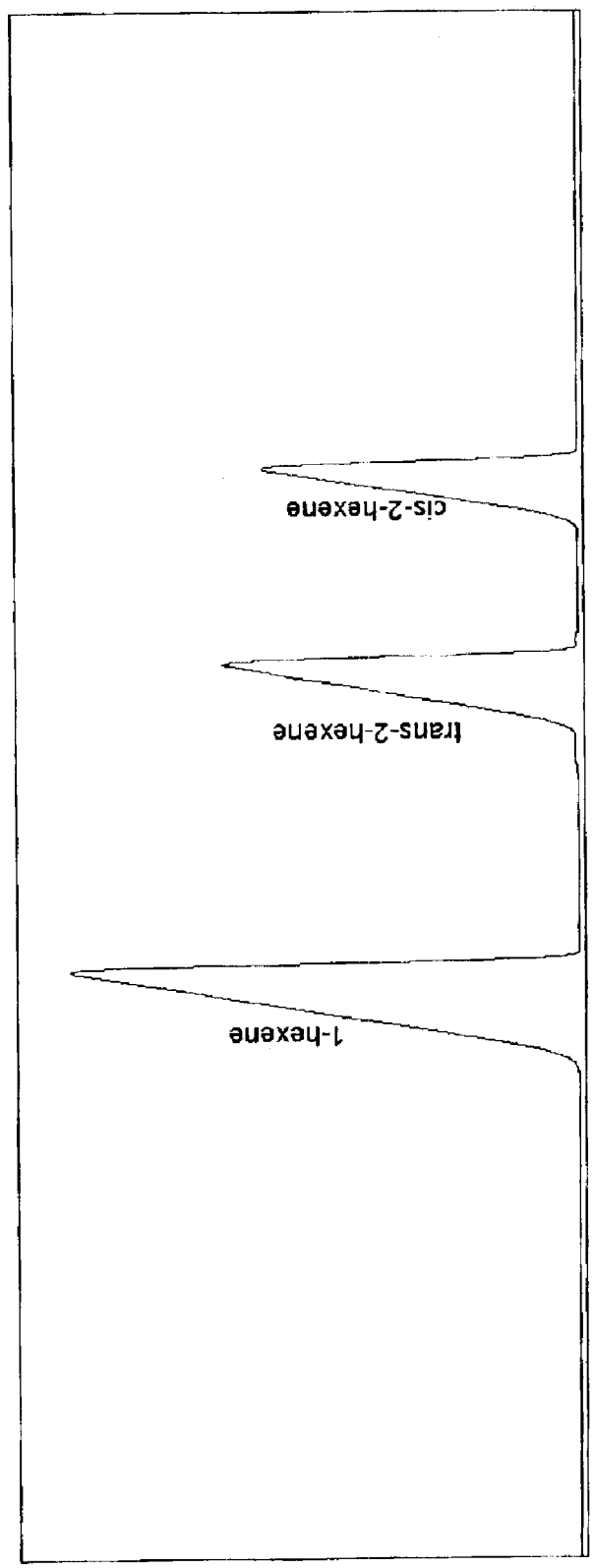
FIG. 1 illustrates the propylene dimer content of an oligomerization product made in accordance with the present invention.

The invention provides ligands and cobalt complexes useful in the production of alpha-olefins via catalysis, and additionally the catalytic dimerization and isomerization of alpha-olefins. The ligands provided are tridentate ligands (or "ligands"), such as that shown complexed with Cobalt in Formula I, which may be identified by the three nitrogen atoms present in the molecule. When producing a metal complex from a tridentate ligand, the ligand may be reacted with the salt of a transition metal, such as Cobalt. The reaction is a coordination reaction between the ligand and the metal salt, which forms a metallic complex such as shown in Formula I. The cobalt complexes employed herein were shown to possess a higher degree of selectivity for producing linear dimers than their iron analogs [4], and are also highly selective for isomerizing the starting material.

The cobalt complex of formula I may be employed in the production of alpha-olefins:

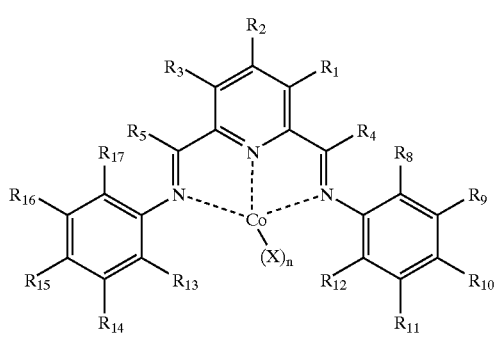

I wherein:

each X is an anion;

n is 1, 2 or 3 so that the total number of negative charges on said anion or anions is equal to the oxidation state of a Co atom present in Formula I;

R1, R2 and R3 are each independently hydrogen, hydrocarbyl, substituted hydrocarbyl, or an inert functional group;

R4 and R5 are each independently hydrogen, hydrocarbyl, an inert functional group or substituted hydrocarbyl;

R9, R10, R11, R14, R15 and R16 are each independently hydrogen, hydrocarbyl, an inert functional group or substituted hydrocarbyl;

R8 and R17 are each hydrogen, fluorine, an inert functional group, a primary carbon group, a secondary carbon group or a tertiary carbon group;

and provided that:

when R8 is a primary carbon group none, one or two of R12, R13 and R17 are primary carbon groups, secondary carbon groups, or inert functional groups, and the remainder of R12, R13, and R17 are hydrogen or fluorine;

when R8 is a secondary carbon group, none or one or two of R12, R13 and R17 is a primary carbon group or a secondary carbon group or an inert functional group and the remainder of R12, R13, and R17 are hydrogen or fluorine;

when $R^8$ is a tertiary carbon group all of R12, R13, and R17 are hydrogen or fluorine; and any two of R8, R9, R10, R11, R12, R13, R14, R15, R16 and R17 vicinal to one another, taken together may form a ring.

The following terms are provided:

A "hydrocarbyl group" is a univalent group containing only carbon and hydrogen. If not otherwise stated, it is preferred that hydrocarbyl groups herein contain 1 to about 30 carbon atoms. The terms "hydrocarbyl" and "alkyl" are equivalent, and may be used interchangeably.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "inert functional group" herein is meant a group other than hydrocarbyl or substituted hydrocarbyl, which does not substantially interfere with any process described herein where the compound in which it is present takes part. Examples of inert functional groups include halo (fluoro, chloro, bromo and iodo), or ethers such as —OR18 wherein R18 is hydrocarbyl or substituted hydrocarbyl. In cases in which the functional group may be near a metal atom, such as R4, R5, R8, R12, R13, and R17, the functional group should not coordinate to the metal atom more strongly than the groups in compounds containing R4, R5, R8, R12, R13 and R17, which are shown as coordinating to the metal cobalt atom, that is they should not displace the desired coordinating group.

By an "alkyl aluminum compound" is meant a compound in which at least one alkyl group is bound to an aluminum atom. Other groups such as alkoxide, oxygen, and halogen may also be bound to aluminum atoms in the compound.

By "neutral Lewis base" is meant a compound, which is not an ion, which can act as a Lewis base. Examples of such compounds include ethers, amines, sulfides, and organic nitrites.

By "cationic Lewis acid" is meant a cation which can act as a Lewis acid. Examples of such cations are sodium and silver cations.

By "relatively noncoordinating (or weakly coordinating)" anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Strauss, Chem. Rev., vol. 93, p. 927–942 (1993), both of which are hereby included by reference. Among such anions are those formed from alkyl aluminum compounds, defined above, and X$^-$, including R19$_3$AlX$^-$, R19$_2$AlClX$^-$, R19AlCl$_2$X$^-$, and "R19AlOX$^-$". Other useful noncoordinating anions include BAF-{BAF= tetrakis[3,5-bis(trifluoromethyl)phenyl]borate}, SbF$_6^-$, PF$_6^-$, and BF$_4^-$, trifluoromethanesulfonate, p-toluenesulfonate, (RfSO$_2$)$_2$N— (wherein Rf is perfluoroalkyl), and (C$_6$F$_5$)$_4$B$^-$.

By formation of an alpha-olefin is meant formation of a compound (or mixture of compounds) of the formula H(CH$_2$CH$_2$)$_q$CH=CH$_2$ wherein q is an integer of 1 to about 18. In most such reactions, a mixture of compounds will result which have differing values of q, and in most reactions to form the alpha-olefins some of the alpha-olefins formed will have q values of more than 18. Preferably less than 50 weight percent, more preferably less than 20 weight percent of the product mixture will have q values over 18. Because the product contains substantial amounts of internal olefins, the alpha-olefin process is selective for making linear products, but not specific for preparing the particular alpha-olefins. These must be separated by a suitable means, for example distillation, and the like.

By "an empty coordination site" is meant a potential coordination site that does not have a ligand bound to it. Thus if an olefin molecule is in the proximity of the empty coordination site, the olefin molecule may coordinate to the metal atom.

By a "primary carbon group" herein is meant a group of the formula —CH$_2$—, wherein the free valence — is to any other atom (the bond represented by the hyphen is to the benzene ring to which the primary carbon group is attached). Thus the free valence — may be bonded to a hydrogen atom, halogen atom, a carbon atom, an oxygen atom, a sulfur atom, etc. In other words, the free valence — may be to hydrogen, hydrocarbyl, substituted hydrocarbyl or a functional group.

Examples of primary carbon groups include —$CH_3$, —$CH_2CH(CH_3)_2$, —$CH_2Cl$, —$CH_2C_6H_5$, and —$CH_2OCH_3$.

By "a ligand that may add to an olefin" is meant a ligand coordinated to a metal atom into which an olefin molecule (or a coordinated olefin molecule) may insert to start or continue a process.

Compounds useful as ligands are diimines of 2,6-pyridinedicarboxaldehyde or 2,6-diacylpyridines, wherein all of the "R" groups are as defined above. Synthesis of these compounds is known in the art, and is further discussed in the Examples section herein.

In preferred compounds of Formula I, and all other preferred compounds in which the following "R" groups appear:
R4 and R5 are methyl or hydrogen; and/or
R1, R2, and R3 are all hydrogen; and/or
R9, R10, R11, R14, R15 and R16 are all hydrogen; and/or
R12 and R17 are each independently methyl, ethyl, propyl or isopropyl, more preferably both are methyl, ethyl, or isopropyl; and/or
each X is a monovalent anion, more preferably selected from the group consisting of halide and nitrile.

It is also preferred that in all compounds in which they appear:
if R8 is a primary carbon group, R13 is a primary carbon group and R12 and R17 are hydrogen;
if R8 is a secondary carbon group, R13 is a primary or secondary carbon group, more preferably a secondary carbon group, and R12 and R17 are hydrogen.

In all specific preferred compounds in which they appear it is preferred that:
R4 and R5 are methyl, R9, R10, R11, R14, R15 and R16 are all hydrogen, and R12 and R17 are both methyl;
R4 and R5 are methyl, R9, R10, R11, R14, R15 and R16 are all hydrogen, and R12 and R17 are both ethyl;
R4 and R5 are methyl, R9, R10, R14, R15 and R16 are all hydrogen, and R12 and R17 are both isopropyl;
R4 and R5 are methyl, R9, R10, R11, R14, R15 and R16 are all hydrogen, and R12 and R17 are both n-propyl;
R4 and R5 are methyl, R9, R10, R11, R14, R15 and R16 are all hydrogen, and R12 and 17 are both chloro; and
R4 and R5 are methyl, R9, R10, R11, R14, R15 and R16 are all hydrogen, and R12 and R17 are both trifluoromethyl.

In all of the above specific compounds it is preferred that X is selected from the group consisting of chloride, bromide and nitrate, and more preferably that it is chloride.

The cobalt complexes may be formed by reacting the appropriate tridentate ligand with a cobalt salt, such as a cobalt halide or a compound such as cobalt [II] nitrate. See Example 1 for the preparation of these cobalt complexes.

In the first process to produce alpha-olefins described herein a cobalt complex of Formula I is contacted with an alpha olefin having at least 3 carbon atoms and a Lewis acid W capable of abstracting $X^-$, hydride or alkyl (R20) from a compound of Formula I to form a weakly coordinating anion, and must alkylate or be capable of adding a hydride ion to the cobalt atom, or an additional alkylating agent or an agent capable of adding a hydride anion to the cobalt atom must be present. The Lewis acid is originally uncharged (for example, not ionic). Suitable Lewis acids include $SbF_5$, $Ar_3B$ (wherein Ar is aryl), $BF_3$, alkylalumoxanes, and trialkylaluminum compounds. Suitable cationic Lewis acids or Bronsted acids include NaBAF, silver trifluoromethanesulfonate, $HBF_4$, or $[C_6H_5NH(CH_3)_2]+[B(C_6F_5)_4]^-$. In those instances in which a compound of Formula I (and similar catalysts which require the presence of a Lewis acid or a cationic Lewis or Bronsted acid) does not contain an alkyl or hydride group already bonded to the cobalt atom, the Lewis acid or a cationic Lewis or Bronsted acid also alkylates or adds a hydride to the cobalt or a separate alkylating or hydriding agent is present, for example, causes an alkyl group (R20) or hydride to become bonded to the cobalt atom.

It is preferred that R20 contains 1 to 4 carbon atoms, and more preferred that R20 is methyl or ethyl.

For instance, alkyl aluminum compounds may alkylate compounds of Formula I. However, not all alkylaluminum compounds may be strong enough Lewis acids to abstract $X^-$ or an alkyl group from the cobalt atom. In that case a separate Lewis acid strong enough to do the abstraction must be present. For instance, $(C_6F_5)_3B$ or $(C_6H_5)_3B$ are useful Lewis acids and could be used in combination with, for example, an alkylaluminum compound such as triethylaluminum.

A preferred Lewis acid, which can alkylate the cobalt, is a selected alkyl aluminum compound, such as $R19_3Al$, $R19AlCl_2$, $R19_2AlCl$, and "R19AlO" (alkylaluminoxanes), wherein R19 is alkyl containing 1 to 25 carbon atoms, preferably 1 to 4 carbon atoms. Suitable alkyl aluminum compounds include alkylaluminoxanes (which are oligomers with the general formula $[R19AlO]_n$).

Metal hydrides such as $NaBH_4$ may be used to bond hydride groups to the Co.

In an embodiment, a method for preparing a polymerization catalyst is provided. The method comprises a coordination reaction between a tridentate ligand such as that of Formula II, and having embodiments as set out previously in this application, and a metal salt. The result of the coordination reaction includes a tridentate metallic complex, such as that of Formula I, and having embodiments as set out previously in this application. The method further comprises generating a metal alkyl or metal hydride species, and contacting the catalyst with one or more monomers under suitable reaction conditions to polymerize the monomer.

In another embodiment of the method for preparing a polymerization catalyst, olefins may or may not be present during generation of a metal alkyl or metal hydride species. In another embodiment, the metal hydride or metal alkyl species is generated by a Lewis acid or a combination of a Lewis acid and alkylating agent. Examples of Lewis acids include $(C_6F_5)_3B$ or $(C_6H_5)_3B$. An example of a metal hydride is $NaBH_4$. In another embodiment, the metal hydride or metal alkyl species is generated by an alkyl aluminum compound such as, for example, triethylaluminum (TEA). In another embodiment, the metal hydride or metal alkyl species is generated by an alkylaluminoxane such as a methyl-aluminoxane (MAO). In another embodiment, the metal hydride or metal alkyl species is generated by a combination of Lewis acids, alkyl aluminums, or alkyl aluminoxanes.

In another process, a cobalt complex of Formula III is either added to the process or formed in situ in the process. Complexes may be added directly to the process or formed in situ. In fact, more than one such complex may be formed during the course of the process, for instance formation of an initial complex and then reaction of that complex to form an active ended oligomer containing such a complex.

Examples of such complexes which may be formed initially in situ include compounds of Formula III:

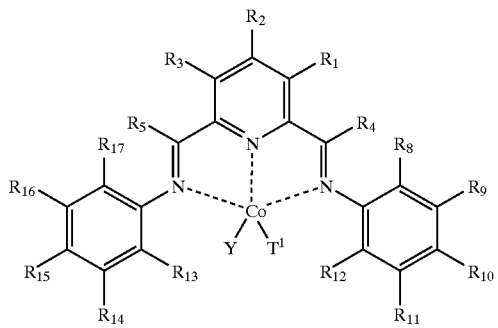

and wherein the "R" substituents are as defined above, T1 is hydride or alkyl or any other anionic ligand into which an alpha olefin having at least 3 carbon atoms can insert, Y is a vacant coordination site, or a ligand capable of being displaced by an alpha olefin having at least 3 carbon atoms.

For instance, a compound of Formula III may be formed by the reaction of a compound of Formula I with a Lewis acid such as an alkyl aluminum compound.

Another method of forming such a complex in situ is combining a suitable cobalt compound such as cobalt chloride, a compound of Formula II:

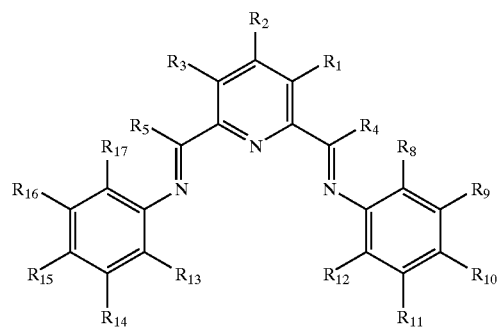

where the R groups are as defined above and an alkyl aluminum compound. Other cobalt salts may be used in which anions similar to chloride are present, and which may be removed by reaction with the Lewis or Bronsted acid. For instance cobalt halides, nitrates and carboxylates (such as acetates) may be used, particularly if they are slightly soluble in the process medium. It is preferred that these precursor cobalt salts be at least somewhat soluble in the process medium.

After the process has started, the complex may be in a form such as a compound of Formula IV:

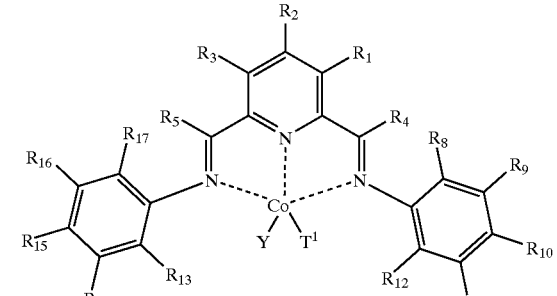

or a compound of Formula V:

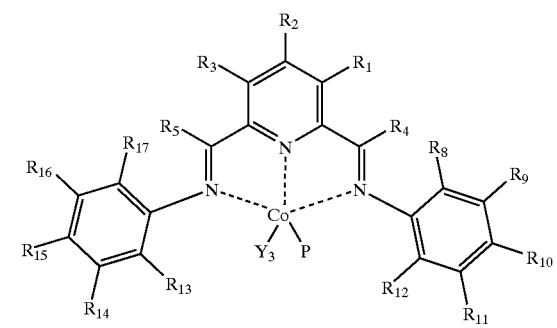

wherein, as before, the R groups are as defined above, and P is an alkyl group. It could at some time, especially at the beginning of the process, be T1. Y3 may be an olefin having at least 3 carbon atoms.

Compounds of formula I, III, IV and V may also be used, in the absence of any "co-catalysts" or "activators" to prepare oligomers. Except for the ingredients in the process, the process conditions, such as temperature, medium, and the like, may be the same as for the other processes.

In all of the processes herein using olefins as a substrate, the temperature at which the processes are carried out is about 0° C. to about 100° C., and preferably about 10° C. to about 50° C.

The processes herein may be run in the presence of various liquids, particularly aprotic organic liquids. The catalyst system, olefin starting material, and oligomer product may be soluble or insoluble in these liquids, but obviously these liquids should not prevent the processes from occurring. Suitable liquids include alkanes, alkenes, cycloalkanes, selected halogenated hydrocarbons, and aromatic hydrocarbons. Specific useful solvents include hexane, toluene, the alpha-olefins themselves, and benzene.

Suitable alpha-olefins to be employed in these processes include propylene, 1-butene, and the like.

The formation of the oligomers as described herein is relatively rapid in many instances, and significant yields can be obtained in less than an hour. Under the correct conditions very high selectivity for an alpha-olefin is shown.

Also, provided herein are oligomerization products, that is the products of an oligomerization reaction, comprising one or more linear oligomers. As used herein, oligomer refers to a molecule of intermediate mass (relative to, for example, a polymer), the structure of which comprises a small plurality of units (e.g., less than about 50) derived from molecules of lower relative mass, for example alpha-olefins, and in particular alpha-olefins having at least 3 carbon atoms (i.e., propylene and heavier). Examples of oligomers include, but are not limited to, dimers, trimers, tetramers, pentamers, and combinations thereof. The term linear oligomer refers to an oligomer wherein the carbon atoms form a straight, unbranched chain or backbone.

In an embodiment, an oligomerization product is formed from the oligomerization of alpha-olefins having at least three carbon atoms, wherein the oligomerization product comprises dimers, at least about 80 weight percent of which (based on the total weight of dimers in the reaction product) are linear. In other embodiments, at least about 90 weight percent of the dimers are linear; alternatively, at least about 95 weight percent of the dimers are linear; or alternatively, at least about 98 weight percent of the dimers are linear. Such linear dimers may be formed from alpha-olefins comprising propylene; alternatively, from alpha-olefins comprising 4 or more carbon atoms; or alternatively, from alpha-olefins comprising propylene and alpha-olefins comprising 4 or more carbon atoms. Examples of such linear dimers include, but are not limited to, hexene, octene, and combinations thereof, including their respective isomers. In other embodiments, such linear dimers may comprise at least about 20 weight percent of the oligomerization product; alternatively, at least about 30 weight percent of the oligomerization product; alternatively, at least about 40 weight percent of the oligomerization product; alternatively, at least about 50 weight percent of the oligomerization product; alternatively, at least about 60 weight percent of the oligomerization product; alternatively, at least about 70 weight percent of the oligomerization product; or alternatively, at least about 80 weight percent the of oligomerization product. Such linear dimers may comprise at least about 10 weight percent 1-olefins; alternatively, at least about 20 weight percent 1-olefins; alternatively, at least about 30 weight percent 1-olefins; alternatively, at least about 40 weight percent 1-olefins; or alternatively, at least about 50 weight percent 1-olefins. In other embodiments, such linear dimers are present in an oligomerization product comprising at least about 20 weight percent 1-olefins; alternatively, in an oligomerization product comprising at least about 30 weight percent 1-olefins; or alternatively, in an oligomerization product comprising at least about 40 weight percent 1-olefins.

In an embodiment, an oligomerization product is formed from the oligomerization of alpha-olefins having at least three carbon atoms, wherein the oligomerization product comprises trimers, at least about 20 weight percent of which (based on the total weight of trimers in the reaction product) are linear. Examples of such linear trimers include, but are not limited to, nonene. In other embodiments, at least about 30 weight percent of the trimers are linear; alternatively, at least about 40 weight percent of the trimers are linear; alternatively, at least about 50 weight percent of the trimers are linear; alternatively, at least about 60 weight percent of the trimers are linear; alternatively, at least about 70 weight percent of the trimers are linear; alternatively, at least about 80 weight percent of the trimers are linear; or alternatively, at least about 90 weight percent of the trimers are linear. In other embodiments, such linear trimers may comprise at least about 10 weight percent of the oligomerization product; alternatively, at least about 20 weight percent of the oligomerization product; alternatively, at least about 30 weight percent of the oligomerization product; alternatively, at least about 40 weight percent of the oligomerization product; or alternatively, at least about 50 weight percent of the oligomerization product. In other embodiments, such linear trimers may comprise at least about 10 weight percent 1-olefins; alternatively, at least about 20 weight percent 1-olefins; or alternatively, at least about 30 weight percent 1-olefins. In an embodiment, linear dimers and trimers comprise at least about 40 weight percent of the oligomerization product.

In an embodiment, an oligomerization product is formed from the oligomerization of alpha-olefins having at least three carbon atoms, wherein the oligomerization product comprises tetramers, at least about 5 weight percent of which (based on the total weight of tetramers in the reaction product) are linear. Examples of such linear tetramers include but are not limited to dodecene. In an embodiment, the alpha-olefins comprise propylene and less than about 70 weight percent of the resulting propylene oligomers have greater than 9 carbon atoms. In other embodiments, at least about 10 weight percent of the tetramers are linear; alternatively, at least about 20 weight percent of the tetramers are linear; alternatively, at least about 30 weight percent of the tetramers are linear; alternatively, at least about 40 weight percent of the tetramers are linear; alternatively, at least about 50 weight percent of the tetramers are linear; alternatively, at least about 60 weight percent of the tetramers are linear; alternatively, at least about 70 weight percent of the tetramers are linear; alternatively, at least about 80 weight percent of the tetramers are linear; or alternatively, at least about 90 weight percent of the tetramers are linear. Such linear tetramers may comprise at least about 5 weight percent 1-olefins.

In an embodiment, an oligomerization product is formed from the oligomerization of alpha-olefins having at least three carbon atoms, wherein the oligomerization product comprises pentamers, at least about 5 weight percent of which (based on the total weight of pentamers in the reaction product) are linear. In other embodiments, at least about 10 weight percent of the pentamers are linear; alternatively, at least about 20 weight percent of the pentamers are linear; alternatively, at least about 30 weight percent of the pentamers are linear; alternatively, at least about 40 weight percent of the pentamers are linear; alternatively, at least about 50 weight percent of the pentamers are linear; alternatively, at least about 60 weight percent of the pentamers are linear; alternatively, at least about 70 weight percent of the pentamers are linear; alternatively, at least about 80 weight percent of the pentamers are linear; or alternatively, at least about 90 weight percent of the pentamers are linear.

In alternative embodiments, various combinations of the linear dimers, trimers, tetramers, and pentamers described herein are present in an oligomerization product. For example, the oligomerization product may comprise linear dimers and trimers; alternatively, linear dimers and tetramers; alternatively, linear dimers and pentamers; alternatively, linear dimers, trimers, and tetramers; alternatively, linear dimers, tetramers, and pentamers; alternatively, linear dimers, trimers, tetramers, and pentamers; alternatively, linear trimers and tetramers; alternatively, linear trimers and pentamers; alternatively, linear trimers, tetramers and pentamers; alternatively, linear tetramers and pentamers.

In alternative embodiments, an oligomerization product comprising one or more of the above linear dimers, trimers, tetramers, pentamers, or combinations thereof may be further converted to alcohols; alternatively, is further converted to a poly alpha-olefin, a poly internal olefin, or combinations thereof; alternatively, is further converted to a carboxylic acid; alternatively, is further converted to a linear alkyl benzene; alternatively, is further converted to a functional drilling fluid; alternatively, is further converted to an alkyl succinic anhydride; alternatively, is further converted to an olefin sulfonate; alternatively, is further converted to an alkane sulfonate; alternatively, is further converted to an epoxide; alternatively, is used as comonomer for production of polyethylene; alternatively, undergoes a purification process such that the weight percent of one or more of the dimers, trimers, tetramers, and pentamers therein is increased; alternatively, is further converted to an alkane sulfonate; alternatively, is further converted to an epoxide; alternatively, undergoes metathesis with ethylene to produce an alpha-olefin from one or more of the dimers, trimers, tetramers, and pentamers having an internal double bond; and combinations thereof, such processes being carried out as would be known to one of skill in the relevant art.

The alpha-olefins made herein may be further polymerized with other olefins to form polyolefins. They may also be homopolymerized. These polymers may be made by a number of known methods, such as Ziegler-Natta-type polymerization, metallocene catalyzed polymerization, and other methods, see for instance World Patent Application 96/23010; see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, p. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylenes, and all of these references are herein incorporated by reference.

The alpha-olefins or internal olefins made herein may be converted to alcohols by known processes, these alcohols being useful for a variety of applications such as intermediates for detergents or plasticizers. The alpha-olefins may be converted to alcohols by a variety of processes, such as the oxo process followed by hydrogenation, or by a modified single step oxo process (the 'modified Shell process'), see for instance B. Elvers, et al., Ed., Ullmann's Encyclopedia of Chemical Technology, 5th Ed., Vol. A18, VCH Verlagsgesellschaft mbH, Weinheim, 1991, p. 321–327, the disclosure of which is herein incorporated by reference.

The products of the instant invention may also be employed as drilling fluid components.

The dimerizations and isomerizations herein may also initially be carried out in the solid state by, for instance, supporting an active catalyst or catalyst precursor on a substrate such as silica or alumina. If a catalyst precursor is, for example, a cobalt halide or nitrate, it may be activated with a Lewis acid (such as W, for instance an alkylaluminum compound) and exposed to an alpha-olefin. Alternatively a solution of the catalyst precursor may be exposed to a support having an alkylaluminum compound on its surface. The support may also be able to take the place of the Lewis or Bronsted acid, for instance an acidic clay such as montmorillonite. Another method of making a supported catalyst is to start a polymerization or at least make a cobalt complex of another olefin or oligomer of an olefin such as cyclopentene on a support such as silica or alumina. All of these "heterogeneous" catalysts may be used to catalyze oligomerization in the liquid phase.

A dimerization process to form linear olefins comprises contacting an alpha-olefin with a cobalt complex of a tridentate bisimine pyridyl-type ligand having single alkyl-substituted or unsubstituted aryl groups that is activated with a bulky non-coordinating co-catalyst such as modified methylaluminoxane, MMAO. Concurrent isomerization of the alpha-olefins to internal olefins of the same carbon number gives a final product comprising linear dimers and internal olefins. Propylene dimerization provides an unexpected high yield of 1-hexene in addition to internal hexenes. The 1-hexene may be removed by distillation. The remaining internal olefins are contacted with a catalyst under isomerization conditions to form additional 1-hexene that is removed continuously by distillation. Propylene is dimerized to a product containing 34% 1-hexene, 47% 2- and 3-hexenes, 15% nonenes and 5% heavies.

Another process may be employed to isomerize alpha-olefins selectively to internal olefins. In an embodiment, an isomerization product formed from alpha-olefins having at least four carbon atoms may include at least about 80 weight percent 2-olefins. In another embodiment where 2-olefins make up at least about 80 weight percent of an isomerization product, the product further includes 3-olefins such that the 2- and 3-olefins together may make up at least about 90 weight percent of the product. In another embodiment, 2-olefins may make up more or less than 80 weight percent of the product, and the 2- and 3-olefins taken together may include at least about 90 weight percent of the product formed from isomerization of alpha-olefins having at least four carbon atoms. Such selective isomerization of alpha-olefins to internal olefins of the same carbon number without dimerization may be achieved by contacting alpha-olefins with the presented cobalt complexes and a coordinating co-catalyst such as diethyl aluminum chloride, DEAC. Other suitable co-catalysts include modified methylalumoxane (MMAO), other aluminoxanes, and ethylaluminum dichloride (EADC). Preferred for the practice of the present invention is DEAC. A molar ratio of Al:Co is preferably about 1:1 to about 200:1.

For 1-Butene Dimerization:

After activation with a co-catalyst, the cobalt catalysts dimerize α-olefins with high productivity (TON ~40,000). The cobalt-produced dimers are extremely linear (>97%) and contain only traces of trimeric species. The cobalt catalysts also have a tendency to isomerize α-olefins, as evidenced by the approximately equal levels of dimerization and isomerization achieved when 1-butene is dimerized. In fact, when the co-catalyst is changed to diethylaluminum chloride, isomerization occurs exclusively to give cis- and trans-2-olefins selectively.

For Propylene Dimerization:

To take advantage of the linear dimerization reaction and to mitigate the effects of feed isomerization, dimerization of propylene was also studied, with remarkable results. GC analysis of the products reveals a step-wise oligomerization process that makes linear hexenes, nonenes, and dodecenes. The hexenes are over 99% linear, and may contain over 50% of the valuable 1-hexene isomer, which can potentially be separated from the 2-hexene byproducts. Catalyst productivity is high (17,000) lbs oligomer/lb Co complex.

EXAMPLES

Abbreviations, Materials, and Sources of Materials

Abbreviations

CPCHEM Chevron-Phillips Chemical Company LP

Materials

Cobalt(II) chloride hexahydrate, 2,6-diacetylpyridine, diethylaluminum chloride, and all aniline derivatives were purchased from Aldrich and used without further purification.

Polymer grade propylene in cylinders with dip tubes for transfer of liquefied gas was purchased from Matheson Gas Products, Inc.

Chevron-Phillips Chemical Company's commercial grade of 1-butene was used without purification.

Chevron-Phillips Chemical Company's 1-hexene was degassed and dried over 3A molecular sieves prior to use.

MMAO 3A was purchased from Akzo Nobel.

TABLE 1

Cobalt Complexes of Formula I

| Complex Number | R12 | R13 |
|---|---|---|
| Ia | Hydrogen | Hydrogen |
| Ib | Methyl | Methyl |
| Ic | Ethyl | Ethyl |
| Id | Isopropyl | Isopropyl |

Example 1

Preparation of Cobalt Complexes of Formula Ia–Id

Precatalyst complexes were synthesized, as were the ligands used to make the complexes.[5-7]

In general, the ligands were prepared by dissolving 2,6-diacetylpyridine and a slight excess (>2 eq.) of the appropriate aniline in methanol, heating the solution for one day under inert atmosphere with a catalytic amount of acetic acid, and recrystallizing the isolated solid from ethanol. The cobalt complexes were prepared by stirring a slight excess of the tridentate ligand with cobalt(II) chloride hexahydrate in THF for at least one day, then adding pentane to the solution and removing the precatalyst complexes by filtration. The complexes were all isolated in near-quantitative yield. Elemental analyses for complexes Ib–Id were carried out to determine the amount of THF in the isolated precatalysts. The solids were heated under vacuum at 40° C. prior to analysis. Complexes Ib and Ic tested positive for an equivalent of THF, but complex Id only contained trace amounts. Elemental analyses are reported as follows:

2,6-bis[1-(2-methylphenylimio)ethyl]pyridine cobalt(II) chloride.THF (Ib). Anal. Calcd. For $C_{27}H_{31}N_3Cl_2OCo$: C, 59.68; H, 5.75; O, 2.94. Found C, 59.00; H, 5.57; O, 2.33.

2,6-bis[1-(2-ethylphenylimino)ethyl]pyridine cobalt(II) chloride-THF (Ic). Anal. Calcd. For $C_{29}H_{35}N_3Cl_2OCo$: C, 60.95; H, 6.17; O, 2.80. Found C, 59.02; H, 5.80; O, 2.37.

2,6-bis[1-(2-isopropylphenylimio)ethyl]pyridine cobalt(II) chloride (Id). Anal. Calcd. For $C_{25}H_{27}N_3Cl_2Co$; C, 61.49; H, 5.92; O, 0.00. Found C, 60.91; H, 5.89; O, 0.16.

Example 2

Isomerization of 1-Hexene to 2-Hexene

Approximately 3.5 liters of 1-hexene was added to a 5 L flask with stirring. The flask was fitted with a reflux condenser. The hexene was degassed overnight. 21 ml of modified methyl aluminum oxane (MMAO) (density 0.73, 7 weight percent Al) was added via syringe, then stirred for approximately 10 minutes. 110 mg of cobalt complex Ia was quickly added to the flask. The mixture then heated up from 22° C. to 39° C. within 2–3 minutes. A bucket of water was used to cool the reaction mixture externally. After 6 hours, 17% of 1-hexene remained. After 3 days, 70% of the mixture was converted to t-2-hexene, 9% was converted to 3-hexene, and 20% was c-2-hexene.

Example 3

Procedure for Dimerization of Liquefied Gases

Under inert conditions, the appropriate cobalt complex was weighed out and added to an NMR tube. A small amount of methylene chloride was added to solublize the complex, and the tube was sealed. The sealed tube was then tied, using copper wire, to the internal cooling coils of a clean, dry Zipperclave™ reactor. The reactor was evacuated and then placed under static vacuum. A glass charger was then used to transfer the cocatalyst to the reactor, and the reactor was back-filled with Argon. The liquefied gas cylinder was pressurized with a head pressure of Argon, and placed on a scale with ±5 g accuracy. Flexible hose was used to connect the gas cylinder to the reactor, and the desired amount of olefin was delivered to the reactor using the head pressure of the cylinder. The reactor was pressurized further with argon to ensure that the olefin remained in the liquid phase. Stirring was begun resulting in breakage of the NMR tube and activation of the catalyst. Reactor temperatures were easily maintained by internal or external cooling, depending on the desired reaction temperature.

Example 4

Procedure for Dimerization/Isomerization of Liquid Olefins

Under inert conditions, the appropriate cobalt precatalyst was added to a dry flask with a stirbar. The alpha-olefin was then added, and rapid stirring was begun to slurry the complex. The flask was placed under a slight argon purge, and the cocatalyst was added via syringe. Temperatures were maintained by use of a water cooling bath.

After slowly adding water to deactivate the catalyst, an internal standard (if necessary) was added. A Hewlett Packard 6890 Series GC System with an HP-5 50 m column with a 0.2 mm inner diameter was used for product characterization. Agilent ChemStation from Agilent Technologies was used to analyze the collected data. GC/MS data were obtained using an Agilent 5973 Benchtop Mass Spectrometer using electron impact ionization interfaced to an HP 6890 gas chromatograph. The GC column was a J&W Scientific DB-5MS, 60 m×0.25 mm i.d.

1-butene was dimerized in liquid phase to further assess the catalyst activity. The results of this reaction are reported below in Table 2. Unlike the analogous tridentate iron systems, these cobalt catalysts produce extremely low levels of methyl-branched heptenes in the octene products, resulting in 97%+linearity in the dimers. Also, the cobalt systems make only traces of butene trimer, in comparison to the iron systems, which produce about 15% trimer. The systems may be activated with relatively low amounts of alumoxane cocatalysts (<100:1 Al:cat molar ratios).

TABLE 2

Dimerization of 1-Butene Using MMAO-Activated Cobalt Complexes Ib–Id

| Cat./Mass (mg) | Al:Co Ratio | C₄ Mass (g) | T (° C.) | Rxn Length (h) | Prod. Mass (g) | % Conversion | Productivity (g dimer/g Co Complex) | % Linear Dimer | D/I Ratio[a] |
|---|---|---|---|---|---|---|---|---|---|
| Ib/50 | 50 | 240 | 35 | 3 | 17 | 7 | 340 | 97 | 0.60 |
| Ic/82 | 200 | 1080 | 20 | 5 | 340 | 31 | 4100 | 98 | 0.72 |
| Ic/160 | 100 | 1500 | 20 | 18 | 157 | 17 | 1600 | 98 | 0.23 |
| Id/160 | 100 | 1500 | 20 | 18 | 124 | 8 | 780 | 98 | 0.14 |

[a]D/I ratio = mass ratio of (dimerized + trimerized butene)/isomerized butene

As a further demonstration of the selectivity of the cobalt catalysts, the undimerized butene was examined. With the iron-based catalysts, the α-olefin feed was only lightly isomerized. With cobalt, however, complexes Ia–Id tended to isomerize the substrate heavily, resulting in the production of substantial quantities of 2-butene in the undimerized olefin. Isomerization occurs when an initial 2,1 (secondary) insertion of olefin is followed by β-elimination with opposite regiochemistry. For iron, initial 2,1 insertions tend to produce branched dimers, indicating that propagation is preferred; cobalt undergoes chain transfer following a 2,1 insertion, resulting in both highly linear dimers and high amounts of isomerization in the feed.

TABLE 3

Oligomerization of Propylene Using MMAO-Activated Cobalt Complexes of Formulas Ib–Id

| Entry | Cat./Mass (mg) | Al:Co Ratio | C₃ Mass (g) | T (° C.) | Rxn Length (h) | Prod. Mass (g) | % Conv. | Mass C₆ (g) | % Linear[a] | % 1-Hexene[b] | Mass C₉ (g)[c] |
|---|---|---|---|---|---|---|---|---|---|---|---|
| 1 | Ib/30 | 100 | 250 | 0 | 5 | 13.7 | 5.5 | 10.4 | 97.4 | 17 | 1.9 |
| 2 | Ib/30 | 100 | 250 | 30 | 5 | 171 | 68 | 115 | 98.8 | 10 | 42.1 |
| 3 | Ic/30 | 100 | 250 | 0 | 5 | 85.1 | 34 | 63.5 | 99.5 | 59 | 17.7 |
| 4 | Ic/30 | 100 | 250 | 20 | 5 | 97.5 | 39 | 70.4 | 99.3 | 50 | 21.4 |
| 5 | Ic/30 | 50 | 250 | 30 | 3 | 196 | 78 | 105 | 99.3 | 37 | 62.1 |
| 6 | Id/30 | 100 | 250 | 20 | 21 | 92.1 | 37 | 68.3 | 99.8 | 53 | 19.3 |
| 7 | Id/30 | 50 | 250 | 35 | 5 | 115 | 46 | 81.6 | 99.6 | 54 | 23.9 |
| 8 | Id/60 | 50 | 250 | 20 | 5 | 134 | 53 | 88.4 | 99.8 | 51 | 33.2 |
| 9 | Id/60 | 50 | 250 | 35 | 5 | 117 | 47 | 81.5 | 99.8 | 53 | 28.3 |

[a]% Linear = % linearity of the C₆ fraction
[b]% 1-Hexene = % 1-hexene in the C₆ fraction
[c]All of the nonene products contained significant quantities of 1-nonenes. Entry 6, for example, contained 34% 1-nonene in the C₉ fraction.

Figure 2:
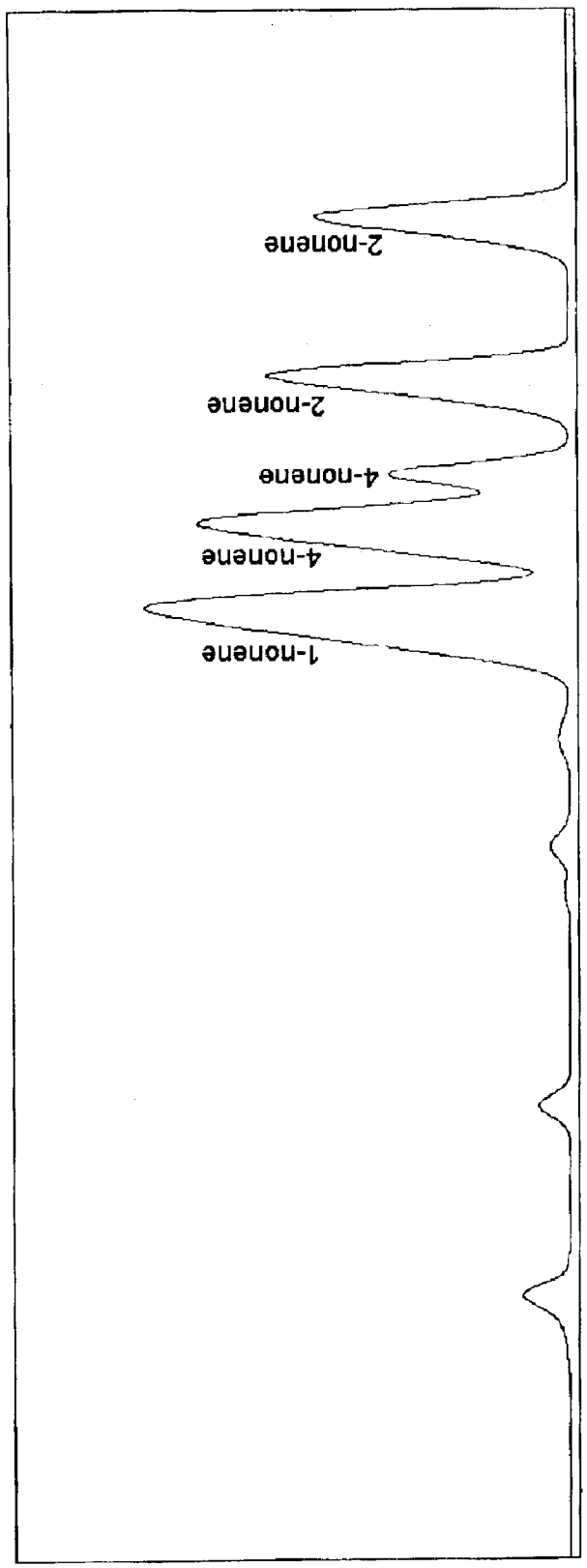
FIG. 2 illustrates the propylene trimer content of an oligomerization product made in accordance with the present invention.

To remove feed isomerization as a possibility, a study of propylene dimerization was undertaken, the results of which are summarized above in Table 3. The cobalt catalysts used in this study are less sterically bulky than those described previously[8]. The experiments in Table 3 employ cobalt catalysts bearing a single ortho substituent on each aryl ring, such as provided in Formulas Ib, Ic, and Id, and the results illustrate several unique trends. First, the catalysts are highly active, with catalyst productivities exceeding 17,000 g product/g Co complex. Second, the catalysts produce not only extremely linear dimers (FIG. 1), but the trimer products are also highly linear (FIG. 2). GC/MS analysis of the C₉ fraction made by catalyst of Formula Ic revealed over 95% linearity in the nonenes, a clear indicator that the C₉ and C₁₂ byproducts are formed by a step growth dimerization process (chain transfer following each insertion). As further evidence for a step growth process, analysis of the linear nonenes by GC/MS also did not reveal any 3-nonenes. Furthermore, the nonenes were even found to contain over 30% 1-nonenes in some instances, as illustrated by FIG. 2, which is a result of co-dimerization of 1-hexene and propylene, with propylene involved in the second insertion step 1-hexene was also made from propylene using these catalysts. Under the conditions employed, it was possible to isolate a propylene-based oligomer in which 70–75% of the products were n-hexenes with over 99.3% linearity. Of these hexenes, over 50% were the 1-hexene isomer, as illustrated by FIG. 1, representing an overall product distribution that contained up to 45% 1-hexene for catalysts systems Ic and Id. With the major by-products in the hexene fraction being cis- and trans-2-hexene, and with only traces of other isomers present, separation of the high value and high purity 1-hexene is possible. In addition, the remaining olefins in the product stream (C₆ plus) are highly linear, and may be used in applications requiring sources of linear internal olefins. Table 4 contains results showing the linearity of various components of an oligomer product made by Catalysts Ib–Id.

TABLE 4

Comparison of Linearity of Oligomers Made by Catalysts Ib–Id.

| Catalyst | C₆ linearity (%) | C₉ linearity (%) | C₁₂ linearity (%) | C₁₅ linearity (%) |
|---|---|---|---|---|
| Ib/MMAO | 99.0 | 96.0 | 94.5 | 93.5 |
| Ic/MMAO | 99.7 | 94.9 | 93.5 | 91.6 |
| Id/MMAO | 99.9 | 94.8 | 87.2 | 75.9 |

The ratio of dimerization to isomerization varies dramatically depending on the activator used. For example, when complexes Ib–Id are activated with MMAO, dimerization and isomerization of the feed are competitive. When diethylaluminum chloride (DEAC) is used, isomerization occurs almost exclusively, resulting in the selective isomerization of 1-olefins to 2-olefins. These data are reported in Table 4. Rather than producing a thermodynamic distribution of internal olefin isomers from the α-olefin feed, the catalysts typically only move the double bond one position. After extended reaction times (up to and including days), the distribution is closer to thermodynamic, but the predominant olefin isomer remains the 2-olefin. When complex Ia, which bears no ortho alkyl groups on the aryl rings, is used as the catalyst, selective isomerization occurs regardless of whether MMAO or DEAC are employed as the activator. Table 5 below provides results on isomerization reactions using 1-hexene as the substrate. Other α-olefins may also be used.

(5) For specific ligand syntheses, see the following references: (a) Small, B. L.; Brookhart, M. J. Am. Chem. Soc., 1998, 120, 7143. (b) Alyea, E. C.; Merrill, P. H. Syn. React. Inorg. Metal-Org. Chem. 1974, 4(6), 535.

(6) For specific Co complex syntheses, see the following references: (a) Edwards, D. A.; Edwards, S. D.; Martin, W. R.; Pringle, T. J. Polyhedron, 1992, 11(13), 1569. (b) Britovsek, G. J. P.; Mastroianni, S.; Solan, G. A.; Baugh, S. P. D.; Redshaw, C.; Gibson, V. C.; White, A. J. P.; Williams, D. J.; Elsegood, M. R. J. Chem. Euro. J., 2000, 6, No. 12, 2221.

(7) For general synthetic details for preparing pyridinebisimine cobalt complexes, see, for example, the following references: (a) Small, B. L.; Brookhart, M.; Bennett, A. M. A. J. Am. Chem. Soc., 1998, 120, 4049. (b) Britovsek, G. J. P.; Gibson, V. C.; Kimberley, B. S.; Maddox, P. J.; McTavish, S. J.; Solan, G. A.; White, A. J. P.; Williams, D. J. Chem. Commun. 1998, 849. (c) Ittel, S. D.; Johnson, L. K.; Brookhart, M. Chem. Rev. 2000, 100, 1169. (d)

TABLE 5

Isomerization of 1-Hexene Using Cobalt Complexes of Formula Ia and Ib

| Cat./Mass (mg) | Cocat. | Al:Co ratio | Olefin/Amt (ml) | T (° C.) | Rxn length (h) | Product distribution (% each isomer) |
|---|---|---|---|---|---|---|
| Ia/10 | MMAO | 115 | 1-hexene/50 | 35 | 2 | 1.9 1-hexene<br>62.4 t-2-hexene<br>34.2 c-2-hexene<br>1.0 other hexenes<br>0.6 dimer |
| Ia/28 | MMAO | 60 | 1-hexene/50 | 5 | 1 | 1.1 1-hexene<br>77.5 t-2-hexene<br>19.9 c-2-hexene<br>0.9 other hexenes<br>0.5 dimer |
| Ia/10 | DEAC | 40 | 1-hexene/50 | 25 | 18 | 1.0 1-hexene<br>62.9 t-2-hexene<br>15.4 c-2-hexene<br>20.5 3-hexenes |
| Ib/27 | DEAC | 40 | 1-hexene/100 | 25 | 72 | 1.0 1-hexene<br>61.2 t-2-hexene<br>15.5 c-2-hexene<br>22.0 3-hexenes<br>0.1 dimer |

All references are herein incorporated by reference.

REFERENCES (1) (a) Chauvin, Y.; Olivier, H. In applied Homogeneous Catalysis with Organometallic Compounds; Cornils, B.; Herrmann, W. Eds.; VCH: New York, 1996; Vol. 1, pp 258–268. (b) Skupinska, J. Chem. Rev. 1991, 91, 613. (c) Parshall, G. W.; Ittel, S. D. In Homogeneous Catalysis, The Applications and Chemistry of Catalysis by Soluble Transition Metal Complexes; John Wiley & Sons, Inc.: New York, 1992; $2^{nd}$ Ed., pp 72.85. (d) Bhaduri, S.; Mukesh, D. In Homogeneous Catalysis, Mechanisms and Industrial Applications; John Wiley & Sons, Inc.: New York, 2000; pp 142–147.

(2) Al-Jarallah, A. M.; Anabtawi, J. A.; Siddiqui, M. A. B.; Aitani, A. M.; Al-Sa'doun, A. W. Catalysis Today, 1992, 14(1).

(3) (a) Olivier-Bourbigou, H.; Chodorge, J. A.; Travers, P. Petroleum Technology Quarterly, 1999, Autumn, 141. (b) Chauvin, Y.; Gaillard, J. F.; Quang, D. V.; Andrews, J. W. Chem. Ind., 1974, 375. (c) Commereuc, D.; Chauvin, Y.; Gaillard, J.; Leonard, J.; Andrews, J. W. Hydrocarbon Process. 1984, 118.

(4) (a) Small, B. L.; Marcucci, A. J. Organometallics, 2001, 20, 5738.

Britovsek, G. J. P.; Gibson, V. C.; Wass, D. F. Angew. Chem. Int. Ed. 1999, 38, 428.

(8) Bennett, A. M. A. U.S. Pat. No. 6,063,881 (DuPont), 2000.

While the present invention has been illustrated and described in terms of particular apparatus and methods of use, it is apparent that equivalent techniques and ingredients may be substituted for those shown, and other changes can be made within the scope of the present invention as defined by the appended claims.

The particular embodiments disclosed herein are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What we claim as our invention is:

1. An oligomerization product formed from alpha-olefins having at least three carbon atoms, comprising: dimers, at least about 90 weight percent of which are linear.

2. The product of claim 1 wherein said alpha-olefins comprise propylene.

3. The product of claim 1 wherein said alpha-olefins comprise alpha olefins having 4 or more carbon atoms.

4. The product of claim 2 wherein said alpha-olefins further comprise alpha olefins having 4 or more carbon atoms.

5. The product of claim 2 wherein at least about 98 weight percent of said dimers are linear.

6. The product of claim 1 wherein said dimers comprise at least about 20 weight percent of the oligomerization product.

7. The product of claim 1 wherein said dimers comprise at least about 50 weight percent of the oligomerization product.

8. The product of claim 1 wherein said dimers comprise at least about 70 weight percent of the oligomerization product.

9. The product of claim 2 wherein said dimers comprise at least about 10 weight percent 1-olefins.

10. The product of claim 2 wherein said dimers comprise at least about 30 weight percent 1-olefins.

11. The product of claim 2 wherein said dimers comprise at least about 50 weight percent 1-olefins.

12. The product of claim 1 wherein the oligomerization product comprises at least about 20 weight percent 1-olefins.

13. The product of claim 1 wherein the oligomerization product comprises at least about 40 weight percent 1-olefins.

14. The product of claim 3 wherein said dimers comprise octene.

15. The product of claim 4 wherein said dimers comprise hexene and octene.

16. The product of claim 2 further comprising trimers, at least about 20 weight percent of which are linear.

17. The product of claim 2 further comprising trimers, at least about 80 weight percent of which are linear.

18. The product of claim 1 further comprising tetramers, at least about 5 weight percent of which are linear.

19. The product of claim 1 further comprising pentamers, at least about 5 weight percent of which are linear.

20. The product of claim 17 further comprising tetramers, at least about 5 weight percent of which are linear.

21. The product of claim 18 further comprising pentamers, at least about 5 weight percent of which are linear.

22. The product of claim 20 further comprising pentamers, at least about 5 weight percent of which are linear.

23. An oligomerization product formed from alpha-olefins having at least three carbon atoms, comprising one or more oligomers selected from the group consisting of dimers, at least about 90 weight percent of which are linear; trimers, at least about 20 weight percent of which are linear; tetramers, at least about 5 weight percent of which are linear; pentamers, at least about 5 weight percent of which are linear; and combinations thereof, wherein the selected oligomers undergo one or more processing steps selected from the group consisting of conversion to alcohols, a poly alpha-olefin, a poly internal olefin, or combinations thereof; conversion to a carboxylic acid; conversion to a linear alkyl benzene; conversion to a functional drilling fluid; conversion to an alkyl succinic anhydride; conversion to an olefin sulfonate; conversion to an alkane sulfonate; conversion to an epoxide; feeding as comonomer for production of polyethylene; purification such that the weight percent of one or more of the dimers, trimers, tetramers, and pentamers therein is increased; metathesis with ethylene to produce an alpha-olefin from one or more of the dimers, trimers, tetramers, and pentamers having an internal double bond; and combinations thereof.

* * * * *